US007837472B1

(12) United States Patent
Elsmore et al.

(10) Patent No.: US 7,837,472 B1
(45) Date of Patent: Nov. 23, 2010

(54) NEUROCOGNITIVE AND PSYCHOMOTOR PERFORMANCE ASSESSMENT AND REHABILITATION SYSTEM

(75) Inventors: Timothy F. Elsmore, Chula Vista, CA (US); Dennis L. Reeves, San Diego, CA (US); Marie Michelle Reeves, Legal Representative, San Diego, CA (US); Kathryn P. Winter, Pensacola, FL (US); Karl E. Friedl, Frederick, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 10/340,473

(22) Filed: Dec. 27, 2002

Related U.S. Application Data

(60) Provisional application No. 60/343,620, filed on Dec. 27, 2001.

(51) Int. Cl.
*G09B 19/00* (2006.01)
(52) U.S. Cl. ...................................... 434/236
(58) Field of Classification Search .................. 434/236, 434/238; 600/300
See application file for complete search history.

(56) References Cited

U.S. PATENT DOCUMENTS

| | | | | |
|---|---|---|---|---|
| 4,464,121 A | * | 8/1984 | Perelli | 434/236 |
| 5,079,726 A | * | 1/1992 | Keller | 702/142 |
| 5,230,629 A | * | 7/1993 | Buschke | 434/236 |
| 5,344,324 A | * | 9/1994 | O'Donnell et al. | 434/258 |
| 5,595,488 A | * | 1/1997 | Gozlan et al. | 434/236 |
| 5,911,581 A | * | 6/1999 | Reynolds et al. | 434/236 |
| 5,961,332 A | * | 10/1999 | Joao | 434/236 |
| 6,066,092 A | | 5/2000 | Cady et al. | |
| 6,113,538 A | * | 9/2000 | Bowles et al. | 600/300 |
| 6,241,686 B1 | * | 6/2001 | Balkin et al. | 600/544 |
| 6,416,472 B1 | | 7/2002 | Cady et al. | |
| 6,435,878 B1 | * | 8/2002 | Reynolds et al. | 434/236 |
| 6,669,481 B2 | | 12/2003 | Winter et al. | |
| 6,712,615 B2 | * | 3/2004 | Martin | 434/236 |
| 2007/0088006 A1 | | 4/2007 | Cady et al. | |

FOREIGN PATENT DOCUMENTS

| | | |
|---|---|---|
| WO | WO 01/54559 A2 | 8/2001 |
| WO | WO 01/54650 A2 | 9/2001 |
| WO | WO 01/72217 A1 | 10/2001 |

* cited by examiner

*Primary Examiner*—Cameron Saadat
(74) *Attorney, Agent, or Firm*—Elizabeth Arwine

(57) ABSTRACT

A computerized Neuropsychological/NeuroCognitive and Psychomotor Performance Assessment and Rehabilitation system is designed for use on handheld computer systems. Components of the system include an executive program, test modules, interpretive and report modules, and supporting utilities. The system provides point-of-use interpretations and result reports. The system is designed for use in clinical settings, occupational medicine, and research. Medical applications include use as a diagnostic, evaluation, and treatment instrument. In industrial settings it can be used as a fitness/readiness for work assessment. The assessment and rehabilitation system also contains modules for use in forensic mental competency, mental and emotional status examinations.

8 Claims, 9 Drawing Sheets

| TEST PARAMETERS/ TEST NAME | SLEEP SCALE | MOOD SCALE | SIMPLE REACTION TIME | RUNNING MEMORY CPT | MATHEMATICAL PROCESSING | LOGICAL RELATIONS | MATCHING TO SAMPLE | MEMORY SEARCH | MATRIX ROTATION | CODE SUBSTITUTION LEARNING | CODE SUBSTITUTION RECALL |
|---|---|---|---|---|---|---|---|---|---|---|---|
| TRIALS | N/A | N/A | 20 | 60 | 20 | 24 | 14 | 40 | 14 | 72 | 36 |
| FEEDBACK | 1 | 0 | 4 | 4 | 4 | 4 | 4 | 4 | 4 | 4 | 0 |
| PAUSELIMIT (SEC) | 60 | 60 | 60 | 60 | 60 | 60 | 60 | 60 | 60 | 60 | 60 |
| REPETITION | 1 | 1 | 1 | 1 | 1 | 1 | 1 | 1 | 1 | 1 | 1 |
| DIFFICULTY | N/A | N/A | 0 | 0 | 0 | 0 | 0 | 6[a] | 1[b] | 9[c] | 9 |
| WARMUP TRIALS | N/A | N/A | 3 | 10 | 5 | 3 | 3 | 3 | 3 | 3 | 0 |
| WU ACCURACY CRIT. | N/A | N/A | 0 | 46 | 35 | 0 | 0 | 0 | 0 | 0 | 0 |
| WU FEEDBACK | N/A | N/A | 0 | 1 | 1 | 1 | 1 | 1 | 1 | 1 | 1 |
| ITIMIN | N/A | N/A | 650 | 750 | 650 | 650 | 650 | 650 | 650 | 750 | 750 |
| ITIMAX | N/A | N/A | 1,350 | 1,250 | 850 | 850 | 850 | 1350 | 850 | 950 | 950 |
| GAPMIN | N/A | N/A | N/A | N/A | N/A | N/A | 5,000 | N/A | 5,000 | N/A | N/A |
| GAPMAX | N/A | N/A | N/A | N/A | N/A | N/A | 5,000 | N/A | 5,000 | N/A | N/A |
| STIM DURATION | N/A | N/A | 5,000 | 300 | 5,000 | 10,000 | 3,000 | 3,000 | 3,000 | 10,000 | 10,000 |
| CHOICE DURATION | N/A | N/A | N/A | N/A | N/A | N/A | 60,000 | N/A | 60,000 | N/A | N/A |
| SEED INCREMENT | N/A | N/A | 0[d] | 0 | 0 | N/A | 0 | 0 | 0 | 0 | 0 |
| SPARELONG1 | N/A | 1[e] | N/A | 1,000[f] | N/A | N/A | N/A | 39 | N/A | 0[h] | 1 |
| SPARELONG2 | N/A | N/A | N/A | N/A | N/A | N/A | N/A | 60[i] | N/A | 1[j] | 0 |
| SPARELONG3 | N/A | N/A | N/A | N/A | N/A | N/A | N/A | N/A | N/A | 0[k] | 4 |
| SPARELONG4 | N/A | N/A | N/A | N/A | N/A | N/A | N/A | N/A | N/A | N/A | N/A |
| SPARESTRING | | N/A | | | | | | | | | |

| RECORD | SUBJECT | TEST | SESSION | REP | TEST/VER | BATTERY | BAT/VER | ARES/VER | SPEED | START | | DUR | STIM | COR | ERR |
|---|---|---|---|---|---|---|---|---|---|---|---|---|---|---|---|
| 1 | NOONE | SLEEP SCALE | 3 | 1 | 0.86 | HEIDELBERG | 1.0 | 0.86 | 2 | 12/27/02 | 11:14:53 | 3 | 0 | 0 | 0 |
| 2 | NOONE | SIMPLE REACTION TIME | 3 | 1 | 0.86 | HEIDELBERG | 1.0 | 0.86 | 3 | 12/27/02 | 11:15:05 | 40 | 20 | 20 | 0 |
| 3 | NOONE | MATHEMATICAL PROCESSING | 3 | 1 | 0.86 | HEIDELBERG | 1.0 | 0.86 | 3 | 12/27/02 | 11:15:59 | 62 | 15 | 13 | 2 |
| 4 | NOONE | MATCHING TO SAMPLE | 3 | 1 | 0.86 | HEIDELBERG | 1.0 | 0.86 | 3 | 12/27/02 | 11:17:07 | 187 | 15 | 13 | 2 |
| 5 | NOONE | LOGICAL RELATIONS | 3 | 1 | 0.86 | HEIDELBERG | 1.0 | 0.86 | 3 | 12/27/02 | 11:20:21 | 93 | 24 | 22 | 2 |
| 6 | NOONE | MEMORY SEARCH | 3 | 2 | 0.86 | HEIDELBERG | 1.0 | 0.86 | 3 | 12/27/02 | 11:22:06 | 112 | 40 | 37 | 3 |
| 7 | NOONE | SIMPLE REACTION TIME | 3 | 2 | 0.86 | HEIDELBERG | 1.0 | 0.86 | 3 | 12/27/02 | 11:24:04 | 39 | 20 | 20 | 0 |
| 8 | NOONE | SLEEP SCALE | 4 | 1 | 0.86 | HEIDELBERG | 1.0 | 0.86 | 4 | 12/27/02 | 12:37:04 | 5 | 0 | 0 | 0 |
| 9 | NOONE | SIMPLE REACTION TIME | 4 | 1 | 0.86 | HEIDELBERG | 1.0 | 0.86 | 4 | 12/27/02 | 12:37:18 | 32 | 20 | 20 | 1 |
| 10 | NOONE | MATHEMATICAL RELATIONS | 4 | 1 | 0.86 | HEIDELBERG | 1.0 | 0.86 | 4 | 12/27/02 | 12:37:59 | 58 | 15 | 14 | 2 |
| 11 | NOONE | MATCHING TO SAMPLE | 4 | 1 | 0.86 | HEIDELBERG | 1.0 | 0.86 | 4 | 12/27/02 | 12:39:05 | 188 | 15 | 13 | 2 |
| 12 | NOONE | LOGICAL RELATIONS | 4 | 1 | 0.86 | HEIDELBERG | 1.0 | 0.86 | 4 | 12/27/02 | 12:42:19 | 92 | 24 | 22 | 2 |
| 13 | NOONE | MEMORY SEARCH | 4 | 1 | 0.86 | HEIDELBERG | 1.0 | 0.86 | 4 | 12/27/02 | 12:44:00 | 100 | 40 | 38 | 0 |
| 14 | NOONE | SIMPLE REACTION TIME | 4 | 2 | 0.86 | HEIDELBERG | 1.0 | 0.86 | 4 | 12/27/02 | 12:45:47 | 38 | 20 | 20 | 0 |
| 15 | NOONE | RUNNING MEMORY | 4 | 2 | 0.86 | HEIDELBERG | 1.0 | 0.86 | 4 | 12/27/02 | 11:43:54 | 125 | 7 | 3 | 4 |

| BATTERY MANAGER | | | |
|---|---|---|---|
| FILE | | | |

| SELECT ARB BATTERY | PRINT | COPY | CLOSE |

PC (ARB BATTERY)

NAME  NEUROCOG

DESCRIPTION  NEUROCOGNITIVE TEST BATTERY

VERSION  2

FEEDBACK  0

NUMBER OF TESTS  9

PDA

| INSTALL ARB |
| LIST PDA BATTERIES |
| DELETE PDA BATTERY |

PDA BATTERIES
NEUROCOG
WARRIOR
COMMANDER
DEMO1
DEMO2

TESTS
SLEEP SCALE
SIMPLE REACTION TIME
CODE SUBSTITUTION
MATHEMATICAL PROCESSING
MATCHING TO SAMPLE
LOGICAL RELATIONS
CODE SUBSTITUTION
MEMORY SEARCH
MOOD SCALE

TEST PARAMETERS

| NAME: | CODE SUB |
|---|---|
| TRIALS: | 36 |
| REPETITION: | 1 |
| FEEDBACK: | 4 |
| SEED INCREMENT: | 0 |
| DIFFICULTY: | 9 |
| WARMUP TRIALS: | 0 |
| WARMUP CRITERION: | 0 |
| WARMUP FEEDBACK: | 0 |
| ITI MINIMUM: | 750 |
| ITI MAXIMUM: | 950 |
| GAP MINIMUM: | 0 |
| GAP MAXIMUM: | 0 |
| STIMULUS DURATION: | 10000 |
| CHOICE DURATION: | 0 |
| PAUSE LIMIT: | 60 |
| SPARE1: | 1 |
| SPARE2: | 0 |
| SPARE3: | 4 |
| SPARE4: | 0 |
| SPARE TEXT: | DELAYED RECALL |

NEUROCOGNITIVE AND PSYCHOMOTOR PERFORMANCE ASSESSMENT AND REHABILITATION SYSTEM

CROSS-REFERENCES TO RELATED APPLICATIONS

This application claims the benefit of priority under 35 U.S.C. 119(e) to provisional U.S. Patent Application No. 60/343,620, filed Dec. 27, 2001 which is incorporated herein by reference in its entirety.

FIELD OF THE INVENTION

This invention relates generally to a computerized test system for assessment of cognitive status, and more specifically to a Neuropsychological/NeuroCognitive and Psychomotor Performance Assessment and Rehabilitation system that is designed for use on a handheld computer system.

BACKGROUND OF THE INVENTION

Computerized test systems are increasingly used for assessment of cognitive status in a wide range of situations that produce changes in brain function. An example of a computerized test battery is the Automated Neuropsychological Assessment Metrics (ANAM) Battery, developed by the U.S. Armed Forces, consists of a library of tests and batteries designed for a broad spectrum of clinical and research applications. This library of computerized tests was constructed to meet the need for precise measurement of cognitive processing efficiency of military personnel in a variety of psychological assessment contexts that include neuropsychology, fitness for duty, neurotoxicology, pharmacology, and human factors research. The tests assess sustained concentration and attention, mental flexibility, spatial processing, cognitive processing efficiency, mood, arousal/fatigue level, and short-term, long-term and working memory.

Computerized test systems may be employed in the evaluation of patients having traumatic head injury, stroke, various disease conditions, rapid decompression, shift work, jet lag, sports injuries, and exposure to toxic chemicals. Presently such test systems are available only on costly, full-featured desktop and notebook computers. The cost and the physical size of the systems render their use impractical in many situations, for example, for on-the-spot evaluation of personnel.

These systems present further disadvantages for testing personnel in the field. Specifically, these systems save results in computer files that must be post-processed for interpretation and for the presentation of the results. This data analysis step frequently delays knowledge of results for days or weeks after the test is completed. The lag between test administration and availability of results has largely limited computerized cognitive testing to research applications where the time delay is not critical. If computerized cognitive tests are to guide decision makers, be they clinicians, industrial supervisors, military commanders, or even the test-takers themselves, results must be available immediately, in a form that is easily understood and that maximizes utility.

Therefore, a need remains for a computerized, flexible, human performance test system that can be used to guide decision making in clinical, industrial, and field settings. A further need remains for a system that generates point-of-use cognitive status reports that provide immediate comparisons with appropriate normative data and/or to the individual's past performance, providing timely feedback to test administrators, supervisors, clinicians, and those taking the tests so that appropriate actions can be taken based upon the test results.

SUMMARY OF THE INVENTION

It is an advantage of the present invention to provide a flexible computerized Neuropsychological/NeuroCognitive and Psychomotor Performance Assessment and Rehabilitation System for testing an individual's performance to guide decision making in clinical, industrial, and field settings. The assessment system can generate point-of-use Cognitive Status Reports (CSR) that provide immediate comparisons with appropriate normative data and/or to the individual's past performance so that timely and appropriate actions can be taken based upon the test results.

It is another advantage to provide a handheld computer, such as Personal Digital Assistants (PDAs), for a portable and cost efficient platform for administration of an assessment and rehabilitation system of the present invention. The portability and relatively low cost of the hand held computer and the test system software provides a highly attractive test platform.

Still another advantage is to provide a computerized neuropsychological testing system that presents different sets of cognitive tests (i.e., test batteries) to maximize utility and validity of the results in order to meet the needs of many different testing situations in varying environments, e.g., evaluation of stroke patients or evaluation of the fitness of a truck driver for duty.

It is another advantage of the present invention to provide a decision aid which presents immediate results in the form of a Cognitive Status Report (CSR) to a user in an easily understood form. The test system algorithms and procedures generate the CSRs for two general types of situations, that is, screening and repeated testing. Screening applications of the present invention utilize demographically appropriate norms for generating a CSR. The goal of testing in these situations is to determine whether the individual being tested is different from the normative group, such that the individual requires a therapy or an intervention. Repeated testing situations require a CSR that indicates significant change from the subject's past performance to objectively evaluate efficacy of therapies or medications.

In the exemplary embodiment of the present invention a computerized Neuropsychological/NeuroCognitive and Psychomotor Performance Assessment and Rehabilitation System, referred to herein as "the assessment and rehabilitation system" or "the system", is designed to operate on handheld computers such as Palm Operating System (OS) and Microsoft Windows CE and Merlin compatible Personal Digital Assistants. The assessment and rehabilitation system also includes software utilities that allow the handheld computer to operate in conjunction with a host desktop or laptop computer for test battery configuration, complex data analysis, and archival data storage.

The assessment and rehabilitation system of the exemplary embodiment of the present invention provides point-of-use interpretations and reports of results of an individual's test. Components of the assessment and rehabilitation system include an executive program, test modules, interpretive and report modules, and supporting utilities. The assessment and rehabilitation system includes test modules for use in medical/clinical settings, occupational medicine, research, and forensic applications. The assessment and rehabilitation system also may be used in medical applications as an instrument for diagnoses, evaluation, and treatment strategies. In industrial settings, the assessment and rehabilitation system may be used as a fitness/readiness for work assessment. The system may also be configured for use in forensic mental competency, mental and emotional status examinations.

Clinical/Medical Applications. The assessment and rehabilitation system of the exemplary embodiment may be configured for medical applications which require diagnoses, evaluation, and treatment. Diagnostic applications of the system may involve neuropsychological assessments in clinical, occupational, and sports medicine. Neuropsychological assessments include mental and emotional evaluation in individuals with neurological disorders such as dementia, head injury, multiple sclerosis, Parkinson's disease, brain tumors, stroke, HIV, anoxia, hypoxia, altitude sickness, decompression sickness, Attention Deficit Hyperactivity Disorder, depression and other mood disorders, schizophrenia and other psychotic disorders, normal pressure hydrocephalus, hydrocephalus, Korsokoff's and other alcohol related disorders, Huntington's disease, hypertension, uremia, diabetes, metabolic disorders, neurotoxic insult, adverse effects of major surgery and other medical procedures, effects of therapeutic pharmacological interventions, drug dependence, and malingering of mental illness and neurological and neuropsychological disorders and impairments.

The system provides objective measurement and evaluation of treatment interventions, and assesses the effectiveness and efficacy of treatments that include surgery, pharmaceutical, and behavioral cognitive retraining/rehabilitation, and occupational therapy. In addition, the system may be used to monitor recovery from neurological and mental diseases, illnesses, and disorders, and fatigue.

Once diagnosis and treatment is completed, the system of the exemplary embodiment may be used for treatment of the subject. The system includes modules for rehabilitation and retraining of cognitive skills and abilities such as attention, memory, executive function that are commonly secondary to brain injury and neurological and metabolic disorders, major surgery, and neurotoxin exposures. The assessment and rehabilitation system also has modules for retraining fine motor skills and abilities that may be secondary to brain injuries and neurological impairment and disease. An example of the latter would be retraining eye-hand-psychomotor coordination for writing rehabilitation purposes.

Research Applications. The assessment and rehabilitation system may be configured for use in a number of research applications such as drug, fatigue and environmental research. Research applications include assessment of cognitive and psychomotor effects of pharmaceuticals, homeopathic compounds and treatments, and cancer chemotherapy and radiation. The system provides objective measurement of recovery from acute or chronic sleep deprivation, and transmeridian desynchronization or "jet lag". The system of the exemplary embodiment also is suitable for use in other environments such as microgravity spaceflight, high altitude hypobaric, underwater hyperbaric, cold and isolated Antarctic, high-g centrifuge and jet cockpit environments, and sports arenas and fields.

Occupational and Forensic Applications. The assessment and rehabilitation system of the exemplary embodiment of the present invention may be utilized to determine fitness and/or readiness for work. The immediate interpretive results provided by the system make it useful for fitness for duty assessments in military field operations, factories, hospitals, the transportation industry including railroad engines, airliner cockpits, and long-haul truck cabs and other workplaces. For example, a pilot may utilize the system in a cockpit to determine whether he or she is sufficiently alert to pilot a plane. The system may also be used in accident investigations by employing the modules of the system that are designed for detection of malingering and forensic mental health and neuropsychological investigations. For example, the system may be used in an investigation of fainting and memory problems following a motor vehicle accident. The system further includes modules to determine emotional and mental status in cases where competency to stand trial is in question.

The exemplary embodiment of the assessment and rehabilitation system is modular and configurable. The system utilizes a number of software modules including the executive program, a registration module, test modules, interpretive modules, report modules, and supporting utilities modules. As discussed briefly above, the test modules may be configured to form any number of test batteries. The test and rehabilitation system collects detailed data on test performance, and utilizes the detailed data to provide immediate Cognitive Status Reports when a test battery is completed. The system also is useful for research with nonhuman primates.

The executive program of the exemplary embodiment controls all critical system functions of the system including test administration, data collection, system security, data encryption, access to restricted system features, and communication with a host computer using radio frequency, serial, USB, IR, or dial-up modem. The executive program further permits recording of notes before and after test administration and allows responses to be recorded using a stylus, response buttons, or voice recognition modalities.

A subject registration module permits secure use of the same test and rehabilitation system by multiple subjects through the use of a Personal Identification Number (PIN) system. For example, a system that is loaded onto a PDA can be available to a workplace employee group to determine whether each of the employees are fit for a particular work assignment. Each employee may use the system utilizing his or her PIN, and the test results are associated with a particular employee each time he or she utilizes the system. The PIN prevents accidental or deliberate manipulations of test results associated with a particular employee. In addition to the immediate report received by the employee, data for the employee is collected over time to evaluate the test results of each employee, as well as the employee group.

The assessment and rehabilitation system of the exemplary embodiment utilizes independent test modules similar to those found in the Automated Neuropsychological Assessment Metrics (ANAM) system and in general mental status examinations. The test modules of the exemplary embodiment are designed to allow specified test options to be modified. For example, the number and spacing of stimulus presentations, the stimulus durations, the task difficulty, etc., may be customized for a particular application. Test modules of the assessment and rehabilitation system include sleep/fatigue scale, mood scale, simple and two-choice reaction time, four choice reaction time, procedural reaction time, Sternberg memory search task, running memory continuous performance task, mathematical processing task, digit set comparison task, logical reasoning-symbolic, Tower of Hanoi (Tower Puzzle), Stroop color/word interference, code substitution (learning and recall), spatial processing task (simultaneous and successive), matching to sample (simultaneous and successive), matrix rotation (simultaneous and successive), tracking (unstable and adaptive), pursuit tracking, switching task, dual task, synthetic work task, tapping (left and right index finger), mental status test, and Aphasia test.

The interpretive and report modules of the exemplary embodiment of the present invention are customized for specific test batteries and applications. The interpretive modules use a variety of criteria for evaluating test performance including demographic norms, clinical subgroup norms, and the subject's own past performances. The Cognitive Status Report (CSR) reports provide immediate feedback when a test battery is completed.

The assessment and rehabilitative system is accompanied by a set of associated component utilities that may be utilized on a host computer. These utilities include communications and data archiving modules and test battery authoring modules. The communications and data archiving modules include programs for retrieving data from the hand held computer, for archiving data in formats compatible with Microsoft Access, Excel, and Oracle, for providing functions for assessing data quality and integrity, and for installing and managing test batteries on the hand held computer. The test battery authoring modules are utilized for configuration of customized test batteries for specific applications. The test battery authoring modules select tests from available test modules, set test sequences and set test options. These customized test batteries are then installed on the handheld computer using a special-purpose utility program.

BRIEF DESCRIPTION OF THE DRAWINGS

The present invention will be better understood from the following detailed description of a preferred embodiment of the invention, taken in conjunction with the accompanying drawings in which like reference numerals refer to like parts and in which:

FIG. 15 illustrates a default parameters table for the ARES tests of a preferred embodiment;

FIG. 16 illustrates a desktop window display of the ARES data management data;

FIG. 17 illustrates a desktop window display of the ARES data management subject information;

FIG. 18 illustrates an ARES data management battery manager screen; and

DESCRIPTION OF THE PREFERRED EMBODIMENT

The following detailed description utilizes a number of acronyms which definitions are typically provided with the first instance of each acronym. For convenience, Table 1 below provides a list of the acronyms and abbreviations and their respective definitions.

TABLE 1

| ACRONYMS AND ABBREVIATIONS | |
|---|---|
| ACRONYM | DEFINITION |
| ANAM | Automated Neuropsychologic Assessment Metrics |
| ARES | ANAM Readiness Evaluation System |
| CSR | Cognitive Status Report |
| IMP | Impulsive Responses |
| ISI | Interstimulus Interval |
| OS | Operating System |
| PDA | Personal Digital Assistant |
| PIN | Personal Identification Number |

Figure 1:
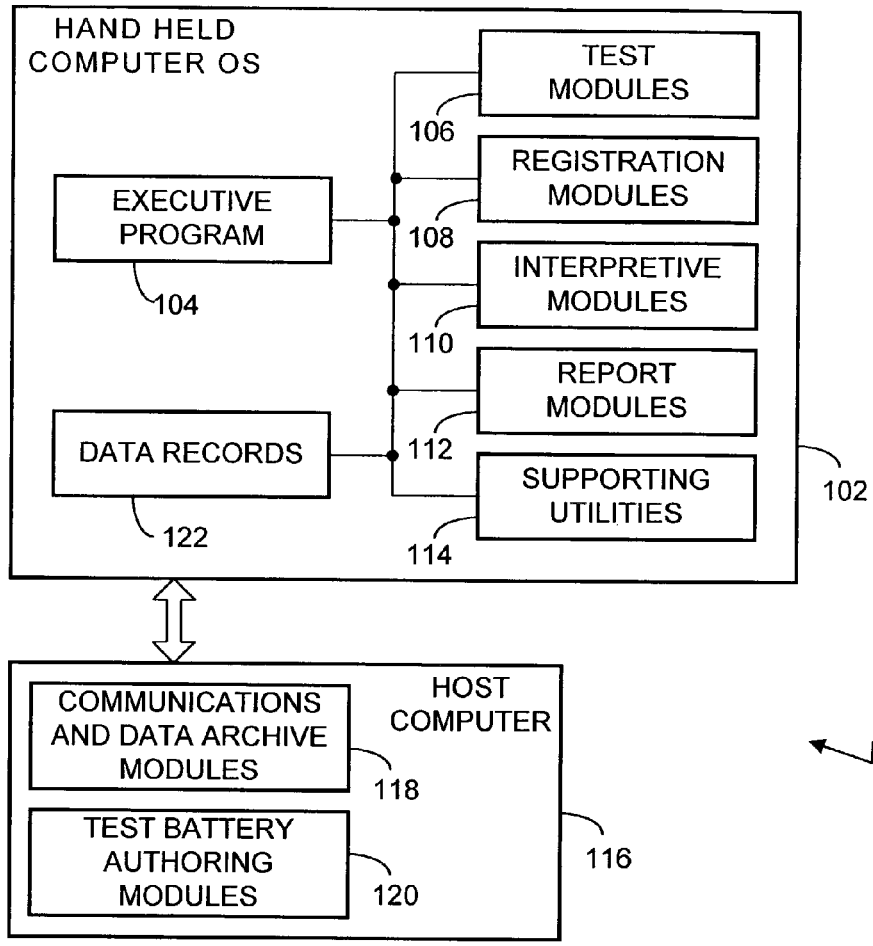
FIG. 1 is a block diagram of the Neuropsychological/NeuroCognitive and Psychomotor Assessment and Rehabilitation Performance System of the preferred embodiment of the present invention.

FIG. 1 illustrates a computerized Neuropsychological/NeuroCognitive and Psychomotor Performance Assessment and Rehabilitation System 100 which is a cognitive testing system designed for use on a handheld computer system 102. Components of the system 100 include an executive program 104, test modules 106, registration modules 108, interpretive modules 110, report modules 112, and supporting utilities 114. The system 100 is designed for point-of-use interpretations and reports of results in clinical settings, occupational medicine, and research. The system 100 is used in medical applications as a diagnostic, evaluation, and treatment instrument. In industrial settings, the system 100 can be used as a fitness/readiness for work assessment. The system 100 also contains modules for use in forensic mental competency, mental and emotional status examinations.

The system 100 is designed to operate on handheld computers 102 such as Palm Operating System (OS) and Microsoft Windows CE and Merlin compatible Personal Digital Assistants (PDAs). The handheld computer 102 of the preferred embodiment is a PDA that utilizes the Palm Operating System (OS), Version 3.5, or later. The system 100 is designed to run on any of the Palm compatible systems, including Visor systems, and on either color or black and white PDA units.

The assessment and rehabilitation system 100 of the preferred embodiment runs test modules 106 in batteries that are designed to meet specific clinical, operational, and/or research goals. The registration modules 108 allow multiple users on a single system 100. The interpretive modules 110 and report modules 112 are customized for specific test batteries and applications. The interpretive modules 110 use a variety of criteria for evaluating test performance including demographic norms, clinical subgroup norms, and the subject's own past performances. The Cognitive Status Report (CSR) reports, generated from the report modules 112, provide immediate feedback when a test battery is completed. The system 100 also includes other utilities, such as supporting utilities 114 on the handheld computer 102 and a desktop data management program on the host computer 116, that facilitate data transfer from the hand held computer 102 to a host computer 116, such as a desktop computer, and test battery installation from the host computer 116 to the hand held computer 102 using a direct serial link, USB, or landline and wireless modems.

Continuing with FIG. 1, the assessment and rehabilitative system 100 of the preferred embodiment is accompanied by a set of associated component utilities that may be utilized on a host computer 116. These utilities include communications and data archiving modules 118 and test battery authoring modules 120. The communications and data archiving modules 118 include programs for retrieving data from the hand held computer, for archiving data in formats compatible with Microsoft Access, Excel, and Oracle, for providing functions for assessing data quality and integrity, and for installing and managing test batteries on the hand held computer. The test battery authoring modules 120 are utilized for configuration of customized test batteries for specific applications. The test battery authoring modules 120 select tests from available test modules, set test sequences, and set test options.

A preferred embodiment of the assessment and rehabilitation system 100 is the ANAM Readiness Evaluation System (ARES) which has been designed to meet the needs for an Operational Medicine portable field neuropsychological and readiness to stand duty assessment instrument. The ARES system 100 utilizes test modules 106 derived from the Automated Neuropsychological Assessment Metrics (ANAM 2001). The ARES system 100 evaluates fatigue and energy levels, the ability to sustain attention/concentration, working memory, spatial processing, and overall cognitive efficiency.

Figure 2:
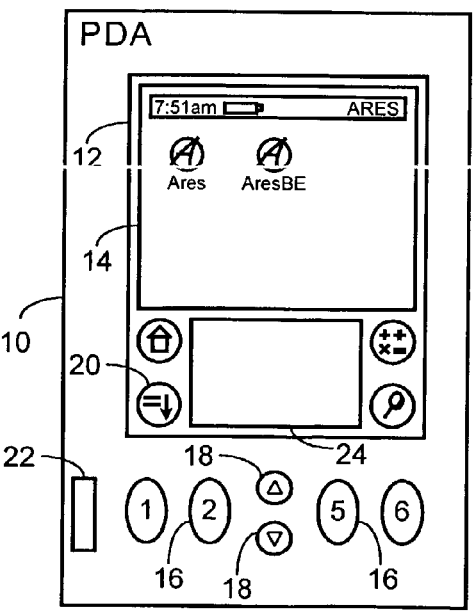
FIG. 2 is an illustration of a personal digital assistant (PDA) for use with an ANAM Readiness Evaluation System (ARES) of a preferred embodiment.

FIG. 2 illustrates ARES 100 loaded onto a Personal Digital Assistant (PDA) 10. The PDA typically has a screen area 12 which may include separate areas for a view screen 14 and a touch screen 24 and touch buttons 20. The PDA of the preferred embodiment has a number of buttons or keys 16, 18, and an on/off switch 22. In the preferred embodiment of ARES 100, the buttons 16, 18 are utilized by the user/subject to "answer" or complete the tasks presented in the view screen 14 as explained further below.

The system of the preferred embodiment 100 implements a subset of the ANAM test modules including Sleep Scale, Simple Reaction Time, Running Memory CPT, Mathematical Processing, Logical Relations, Matching To Sample, Memory Search, Mood Scale, Matrix Rotation, and Code Substitution. These test modules 106 are combined to form five standard test batteries for the ARES embodiment of the invention includes the NeuroCog, the ARES Commander, the ARES Warrior, and a Demonstration 1 and Demonstration 2 module, as shown in Table 2. The two demonstration batteries present a small number of stimuli to illustrate the tests. The executive program 104 of the preferred embodiment creates the Commander battery and the two demonstration batteries if they do not exist when the program is launched. The other batteries may be installed, if desired, utilizing the host computer 116 or another handheld computer 102. In another embodiment, the executive program can create any number of standard test batteries Sleep Scale. Sleep scale is a scale consisting of seven statements that describe how the user feels with respect to alertness or sleepiness. The statement stimulus set includes the sleep scale statements
  1. Fully alert and energetic
  2. Able to concentrate, not at peak
  3. Relaxed, not fully alert
  4. Difficulty concentrating
  5. Tired, can't concentrate
  6. Sleepy, weary, fighting sleep
  7. Very sleepy, falling asleep A statement selection highlighter is initialized to highlight the middle statement (Difficulty concentrating) on the view screen 14 when the test begins. The sleep score stored in the system 100 data records 122 is the length of time, in seconds, that is used to select a statement, and the number of times the selection buttons 16, 18 are depressed on the hand held computer.

TABLE 2

STANDARD TEST BATTERIES

| | NeuroCog | ARES Commander | Ares Warrior | Demo 1 | Demo 2 |
|---|---|---|---|---|---|
| 1 | sleep scale | sleep scale 1 | sleep scale | sleep scale | code substitution (learning) |
| 2 | mood scale 2 | simple RT | simple RT1 | mood scale | matching to sample |
| 3 | simple RT | running memory | math processing | simple RT | running memory |
| 4 | code substitution (learning) | | match to sample | math processing | memory search |
| 5 | math processing | | logical relations | | logical relations |
| 6 | matching to sample | | | | matrix rotation (simultaneous) |
| 7 | logical relations | | | | matrix rotation (successive) |
| 8 | code substitution (recall) | | | | code substitution (recall) |
| 9 | memory search | | | | |

Simple Reaction Time (SimpleRT). Simple reaction time provides a measure of pure reaction time as will as a means to partial out the effects of "motor" or "peripheral nerve conduction velocity" times from actual cognitive processing time. The test presents a simple stimulus on the screen 14 of the hand held computer 10. The user is instructed to press a specified response key 16, 18 each time the stimulus is presented.

Mathematical Processing. The mathematical processing module presents arithmetic problems to the user. The user is instructed to read and calculate from left to right to determine whether the answer is greater-than or less-than the number five. Fifty percent (50%) of mathematical problems will have an answer "greater than 5", and the other fifty percent (50%) will have and answer of "less than 5." The answer is never equal to five. The mathematical equations are either an a+b−c combination or an a−b+c combination. The order is randomly determined prior to stimulus generation, and is based on an array of elements that matches the number of problems to be presented. The mathematical equations are created utilizing three different randomly selected digits ranging from 1 to 9. are randomly selected. If the solution to the equation is less than one, greater than ten, or equal to five, then another set of digits are selected. These steps are applied to construct each problem for a given test session.

Matching to Sample. The matching to sample module is a test in which the user is required to match a block pattern from memory. A 4×4 grid (the "sample") is represented by a 16-bit word in which each bit represents one cell, and eight of the bits are randomly set. The sample grid is displayed to the user. After a pre-specified time interval, two comparison grids are presented side by side, with one of the comparison grid matching the sample grid. Comparison grids are generated by copying the sample grid. The non-matching comparison grid is generated by randomly exchanging one of the set and non-set bits. Therefore only two cells will be different. The sample and comparison patterns that are one of 24 "easy" patterns, that have been defined through trial and error alpha test trials, are discarded from the test. Fifty percent (50%) of the trials are selected to be correct for the left comparison box and the other half for the right comparison box.

Logical Relations. The logical relations module is a linguistic task that requires the ability to determine whether various simple sentences correctly describe the relational order of two symbols. The stimulus set of the preferred embodiment consists of twelve relational statements and two symbol pairs for a total of twenty-four trials as shown in Table 3. During the test, all 24 statements are presented. The order of presentation is determined by pseudo-random selection with a random number seed that matches the test session number, or session number plus the seed increment number.

TABLE 3

LOGICAL RELATIONS

| Statement | Symbols | Correct answer |
| --- | --- | --- |
| # is first | # & | TRUE |
| # is first | & # | FALSE |
| & is first | # & | FALSE |
| & is first | & # | TRUE |
| # is second | # & | FALSE |
| # is second | & # | TRUE |
| & is second | # & | TRUE |
| & is second | & # | FALSE |
| # comes after & | # & | FALSE |
| # comes after & | & # | TRUE |
| & comes after # | # & | TRUE |
| & comes after # | & # | FALSE |
| # comes before & | # & | TRUE |
| # comes before & | & # | FALSE |
| & comes before # | # & | FALSE |
| & comes before # | & # | TRUE |
| # is not first | # & | FALSE |
| # is not first | & # | TRUE |
| & is not first | # & | TRUE |
| & is not first | & # | FALSE |
| # is not second | # & | TRUE |
| # is not second | & # | FALSE |
| & is not second | # & | FALSE |
| & is not second | & # | TRUE |

Memory Search. The memory search module presents a "memory set" of letters displayed on the screen. The user is asked to view the memory set until it is memorized. After the memory set is learned, the user presses a response key to begin the test. During the test, single letters are displayed, and the user must indicated whether the single letters match any of the memory set letters. Each successive administration of the test uses a unique memory set. Memories set letters are selected pseudo-randomly based on the session number from the list of ABCEFGHIJKLMQRSTUXYZ. The memory set size is a maximum of eight letters, and the standard test uses a set of six letters. Positive probe letters are equally likely to match any of the memory set letters, i.e., fifty percent (50%) of the test stimuli will match the memory set letters. Negative probe letters are randomly selected from the remaining set of fourteen (14) non-memory set letters. The negative set size is equal to the positive set size. Further, positive and negative probes are first presented in a random order until each letter is presented. This procedure is continued until the test is completed. The number of stimuli in a given test is restricted to multiples of the sum of the number of letters in the positive and negative sets. For example, in the standard version, there will be six (6) positive and six (6) negative letters, the sum of which is twelve (12). Therefore the number of stimuli presented in the test must be a multiple of twelve.

Running Memory Continuous Performance Test. In the running memory module, the user must monitor a randomized sequence of stimuli digits ranging from 0 to 9. The user presses a specified key if the number on the screen matches the number that immediately preceded it. A different key is pressed if the number does not match the number that immediately preceded it. The first number is pseudo-randomly chosen from 0 to 9. On subsequent trials, if a number has been repeated four times, then a new number is selected. If a number has not been repeated four times, then a random number is chosen from 0 to 999. If the number is less than 456, then a number is displayed that does not match the number that immediately preceded it. Otherwise the number will match the preceding number. The above process produces fifty percent (50%) matching trials with no more than four repetitions of a given stimulus. The executive program counts the number of times matching numbers are presented.

Mood Scale. The Mood Scale module asks the subject to rate thirty-six words describing feelings on a scale from 0 to 10. The words are presented on the view screen 14 in the order shown in Table 4. These words represent six mood categories as shown in Table 5. 3. A visual-analog scale is initialized to a center (5) position when each word is presented. Each word is presented for a minimum of 1 second. Ratings and response times for each word are recorded.

TABLE 4

MOOD SCALE WORD ORDER

1. Miserable
2. Uneasy
3. Inactive
4. Energetic
5. Discouraged
6. Grouchy
7. Lively
8. Good
9. Enraged
10. Annoyed
11. Depressed
12. Alarmed
13. Insecure
14. Weary
15. Alert
16. Lazy
17. Content
18. Cheerful
19. Sad
20. Downcast
21. Satisfied
22. Angry
23. Gloomy
24. Afraid
25. Furious
26. Drowsy
27. Nervous
28. Irritated
29. Tired
30. Spirited
31. Pleased
32. Active
33. Happy
34. Vigorous
35. Anxious
36. Sluggish

TABLE 5

MOOD CATEGORIES

| Vigor | Happiness | Depression | Anger | Fatigue | Anxiety |
|---|---|---|---|---|---|
| Energetic | Good | Miserable | Grouchy | Inactive | Uneasy |
| Lively | Content | Discouraged | Enraged | Weary | Alarmed |
| Alert | Cheerful | Depressed | Annoyed | Lazy | Insecure |
| Spirited | Satisfied | Sad | Angry | Drowsy | Afraid |
| Active | Pleased | Downcast | Furious | Tired | Nervous |
| Vigorous | Happy | Gloomy | Irritated | Sluggish | Anxious |

Matrix Rotation. The Matrix Rotation module utilizes a first 4×4 grid that is constructed as described above for Matching to Sample. The first grid is presented to the subject on the view screen 14 of the PDA 10. A second grid then is constructed that is either identical to the first, or has one cell moved, as described above for the comparison grid in Matching To Sample. Fifty percent (50%) of the new grids are altered. The second grid is then rotated. After a pre-specified time period, the subject is presented with the first grid and the rotated second grid. The subject must then determine whether the first gird and the rotated second grid are either the same or different.

Figure 13:
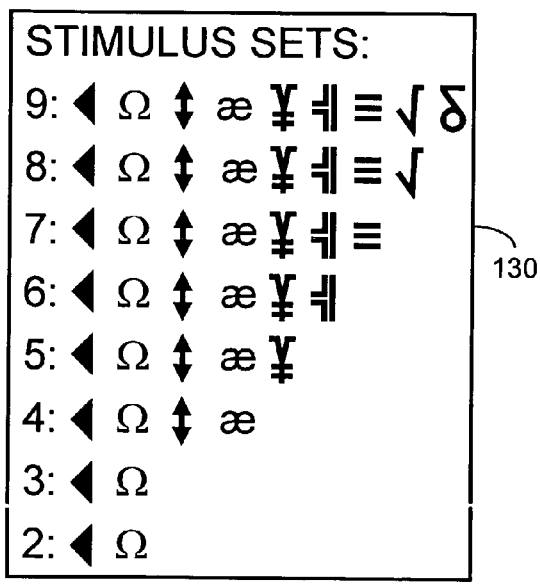
FIG. 13 illustrates stimulus sets of a code substitution test of an assessment and rehabilitation system of the preferred embodiment.

Code Substitution Code substitution consists of from two to nine symbols selected from the stimulus sets 130 illustrated in FIG. 13. The default set size is nine. The set size is determined by the value of the "difficulty" variable in a test parameter list. In each session, each symbol is randomly paired with a digit, from one (1) to the set size. The random number generator is seeded with the session number. Thus, if the learning and delayed versions of the test occur in the same battery, they will have the same symbol/digit pairings. The session type is determined by the value of the "sparelong1" variable in the test parameter list 140, as illustrated in FIG. 15, where 0=Learning, 1=Delayed.

Figure 14:
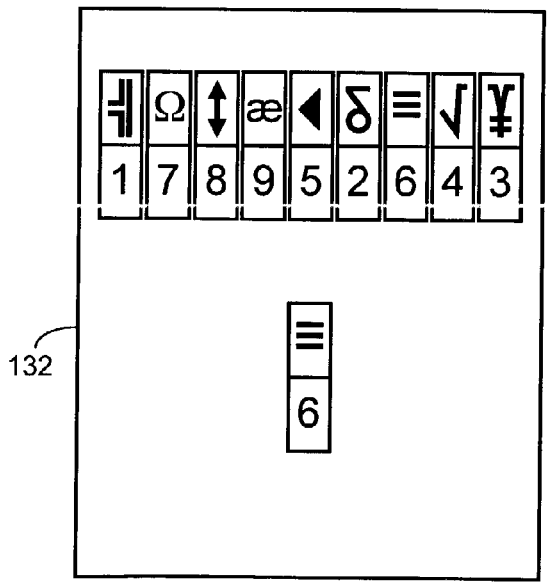
FIG. 14 shows symbol digit pairings for the code substitution test.

In a "learning" version of the module, the symbol/digit pairings are displayed on the top of the view screen 14, and remain there for the entire session. On each trial, a single symbol/digit pair is presented below the display 132 showing all pairs, as shown in FIG. 14. The number of trials is set to eight times the set size, with six correct and two incorrect symbol/digit pairs presented for each symbol. In a "delayed (recall)" version of the program, the correct symbol/digit pairings are not shown, and a single pair is presented on each trial. The number of trials is set to two times the set size, with one correct and one incorrect symbol/digit pair presented for each symbol.

The ARES system 100 uses a standard C-language data structure to specify parameters for all tests. The test parameters for the preferred embodiment of the invention are summarized in Table 6, where "char" is a text variable (string), UInt16 is an unsigned 16-bit integer, and UInt32 is an unsigned 32-bit integer. Feedback values are 0=none, 1=correct/error after each response, 2=RT after each response (ms), and 4=percentage correct, mean correct RT at end of test. These values are not mutually exclusive and may be added to produce more than one type of feedback. For example, a feedback value of 5 will produce correct/error feedback on each trial, and percentage correct and mean correct RT at the end of the test. Warm-up criterion is the number of correct "y" out of a first "x" warm-up trials. The format is "xy" is used to indicate that x is the number of correct responses, and y is a number less than or equal to the number of warm-up trials. Both x and y must be less than 10, and x must be less than or equal to y. For example, "35" would mean 3 correct of first 5 trials. Warm-up feedback is defined as immediate stimulus feedback where 0=none, 1=Corr/Err, 2=RT (ms), 1+2=both. FIG. 16 shows the default values for each test parameter utilized in the preferred embodiment.

TABLE 6

PARAMETER SPECIFICATION

```
struct testparameters {
char¹ testname[25];
char testversion[5];
UInt16 trials;           //scheduled number of trials
UInt16 session;          //from subject record
UInt16 feedback;         // within test and end-of-test feedback²
UInt16 pauselimit;       //timeout for no response (sec)
UInt16 repetition;       //within-battery rep
UInt16 difficulty;       //difficulty level
UInt16 warmuptrials;     //no-data warm-ups
UInt16 warmupcriterion;  //#correct out of first specified # of test trials³
UInt16 warmupfeedback;   //immediate feedback during warmup trials⁴
UInt32 itimin;           //minimum intertrial interval (ms)
UInt32 itimax;           //maximum intertrial interval (ms)
UInt32 gapmin;           //minimum sample-choice interval (ms)
UInt32 gapmax;           //maximum sample-choice interval (ms)
UInt32 stimduration;     //maximum stimulus presentation time (ms)
UInt32 choiceduration;   //maximum choice presentation time (ms)
UInt32 seedincrement;    //added to session number
UInt32 sparelong1;
UInt32 sparelong2;
UInt32 sparelong3;
UInt32 sparelong4;
char sparestring[50];    //
};
```

A table of values is setup prior to any stimulus presentation. This table includes one hundred (100) time periods where each time period is equal to the minimum Interstimulus Interval (ISI) plus a random portion ranging from 0% to 100% of the difference between the minimum and maximum ISIs. The random number generator is seeded at the beginning of each session by the session number plus seed increment value which is defined in each test in the parameters table and is usually set to 0. The ISI may be extended by inappropriate responses that may occur between stimulus presentations. That is, the ISI is determined as stated above, but is reset if a response button is depressed prior to presentation of the next stimulus. For example, if a subject continuously presses a response button at the rate of 700 ms between a stimulus presentations during the Simple RT test, he or she can delay the presentation of the next stimulus indefinitely. If a response button is held in the depressed position, the ISI will not begin until it is released. Therefore, holding down a response button will prevent progression of the test by preventing subsequent display of the next stimulus. Impulsive responses (IMPs) are defined as responses that occur less than 130 ms after stimulus display. This applies to all tests. Inter-trial interval (ITI) responses are those that occur between stimulus presentations, and are also recorded. The default parameters of FIG. 15 include an "itimin" and an "itimax" for each test excluding the sleep scale and the mood scale.

FIG. 15 is a table of the test parameters 140 for each of the test modules utilized in the assessment and rehabilitation system 100 of a preferred embodiment. The parameters are further defined by footnotes (a) through (k) as follows: (a) for memory search difficulty, the number of letters in the memory set range from 2 to 8; (b) for matrix rotation difficulty, 1=90 degrees, 2=180 degrees, 4=random 90 or 180 degrees, and an addition of 8 to these values converts to a successive problem; (c) for code substitution difficulty, the set size varies from 2 to 9, with values less than 2 or greater than 9 defaulting to 9; (d) in simple reaction time, for a repetition=2, the seed increment is 100; (e) mood scale bitwise options are 1=enable touch screen 20, 24 on the PDA 10, 2=enable prompting tone (3 second intervals); (f) for running memory CPT, the time allowed for responses is in milliseconds (ms); (g) for memory search, the minimum memory set observation time is in seconds (sec); (h) for code substitution, the sparelong 1 setting determines the mode, where 0=learning, 1=delayed (i.e. recall); (i) for memory search, the maximum memory set observation time is in seconds (sec); (j) for code substitution, sparelong2 is a bitwise setting for extended feedback, where 0=none, 1=visual feedback (red rectangle) for errors, 2=auditory feedback for errors; and (k) for code substitution, sparelong3 determines the number of presentations of each symbol where 0=default (learning, 8, 6 correct, 2 incorrect; recall 2, 1 correct, 1 incorrect).

Referring again to FIG. 2, the ARES embodiment of the Neuropsychological/NeuroCognitive and Psychomotor Performance Assessment and Rehabilitation System 100 may be installed on a personal digital assistant 10 utilizing a personal or host computer 116. In one embodiment of the invention, a host computer data management program includes a folder containing ARES files for installation on the PDA 10. The ARES software of a preferred embodiment requires a PDA with the Palm OS, version 3.5 or higher and a Hot Sync cradle or cable.

ARES includes a number of Palm Operating System (OS) modules as listed in Table 7. As shown in FIG. 2, only two programs, an ARES executive program and an ARES back end program appear on the view screen 14 of the PDA 10. In most applications that utilize the assessment and rehabilitation system 100, only the ARES executive program is used. The ARES executive program controls the subject registration modules, the execution of the test batteries of test modules, the review of data on the PDA, and the communication with a host PC.

TABLE 7

ARES PALM OS MODULES

PROGRAM

| | FUNCTION |
|---|---|
| Ares.prc | ARES Executive |
| AresSub.prc | Subject Registration |
| AresBE.prc | Performance Index Calculation |
| | TEST MODULES |
| AresCS.prc | Code Substitution |
| AresLR.prc | Logical Relations |
| AresMO.prc | Mood Scale |
| AresMP.prc | Mathematical Processing |
| AresMR.prc | Matrix Rotation |
| AresMS.prc | Matching to Sample |
| AresRM.prc | Running Memory |
| AresRT.prc | Simple Reaction Time |
| AresSS.prc | Sleep Scale |
| AresST.prc | Memory Search (Sternberg) |

Figure 3:
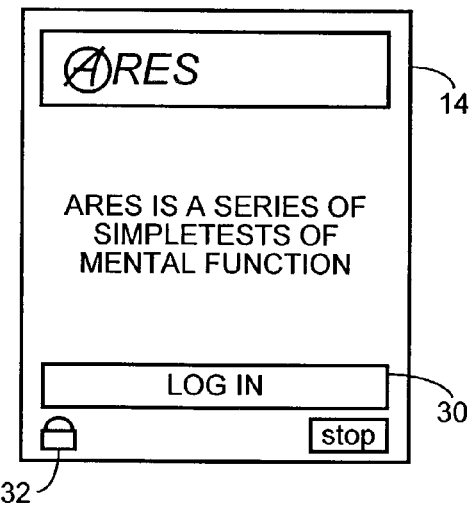
FIG. 3 is a diagram of a log in view screen for a preferred embodiment of an ANAM Readiness Evaluation System.

ARES is designed to allow more than one subject to use a single PDA utilizing the registration modules 108. Registration of each subject also allows different subjects to use different test batteries. Each subject must be registered prior to running an actual test battery. FIG. 3 illustrates a main screen of a preferred embodiment of ARES which appears when the subject taps the ARES executive program in the view screen 14. To register a new subject or edit an existing subject, the subject taps the padlock icon 32 in the lower left corner of the view screen 14. A screen appears requesting a password. If the password is valid, an ARES subject database screen 36 allows a user/subject to add 38, edit 42, or delete 44 subject information 46. The ID's of all currently registered subjects will be listed in the text box 46. If all subjects do not show in the box, tapping the arrow(s) 48 at the right of the text box 46 scrolls the subject list. The ARES subject database screen 36 can only be accessed through the ARES executive module in order to maintain control over the registration process. The required password protects subjects from viewing or modifying the registration information or test results of other subjects using the same PDA 10.

Figure 6:
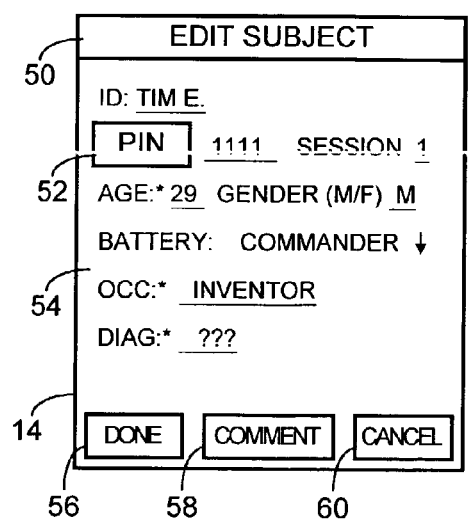
FIG. 6 illustrates an ARES edit subject view screen.

FIG. 6 illustrates the edit subject screen 50 and fields 54 used to register the subject, to edit the subject information, and to select a test battery. The identification field is the subject identification code and is used during subject Log In procedures. The identification code also is used to identify all of the subject's records in the database. The personal identification number 52 (PIN) is used to verify a subject's identity when running a test battery. Tapping the PIN button displays an easy-to-use numeric keypad for entering PINs. The session number indicates the latest session recorded. This variable is automatically set, and typically is not changed. The battery is select from a list shown by tapping a down arrow. The selected battery will be associated with the subject so that the battery is automatically run once the subject logs onto the system 100. The occupation field may be used to record the occupation "other category" variables such as military rank of the subject. The diagnosis field may be used to record a subject's diagnosis category.

The edit subject screen 50 of the preferred embodiment also provides access to a comment entry screen using a "Comment" button 58. Values are entered into the fields utilizing Graffiti, or the mini-keyboard that can be displayed by tapping a keyboard icon at the lower left corner of the graffiti screen 24, as illustrated in FIG. 2. A done button 56 or a cancel button 60 are provided to exit the edit subject screen 50.

Administering an ARES test battery. A subject utilizes ARES by tapping the ARES Executive program icon displayed on the ARES screen of FIG. 1. The subject then taps the Log In button 30 to proceed to the subject database screen 36 which lists the registered subjects. The subject enters his or her PIN 52, and if the correct PIN is entered, a start screen appears (not shown). Tapping a start button (not shown) on the start screen begins battery administration.

Figure 7:
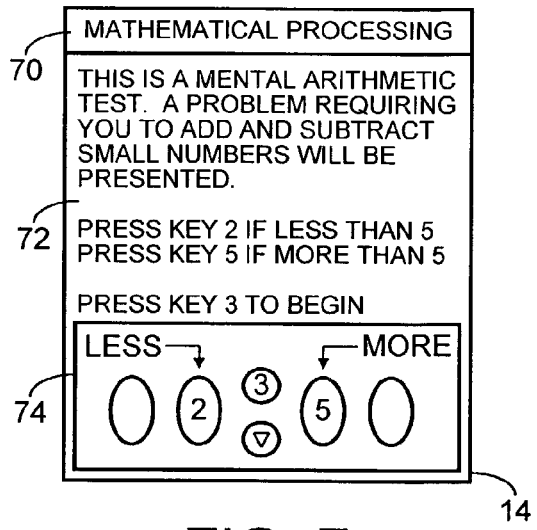
FIG. 7 illustrates a mathematical processing instruction view screen.

The ARES tests of the preferred embodiment are designed to use only the keys 16, 18 at the bottom of the PDA 10 for user/subject input. However, in other embodiments of the invention, the touch-sensitive screen may be used during the tests. The PDA 10 may be held with both hands using the thumbs to manipulate the keys 16, 18 for taking ARES tests. Each test begins with a screen showing a brief explanation of how the test operates. FIG. 7 illustrates a view screen 14 for a mathematical processing test 70. All of the tests provide a graphic representation 74 of the keyboard at the bottom of the screen 14 with the active keys and their meanings shown. In general, the top center key "3" is used to start a test, and the keys "2" and "5" to either side of the center are used to enter responses to the test items.

With the exception of Sleep Scale and Mood Scale, the tests can be programmed to begin with a brief "warm-up". The "warm-up" ensures that the instructions are understood. For two of the tests, Mathematical Processing and Running Memory, a mastery criterion can be specified and required to be met by the subject before allowing administration of the test proper. If the criterion is not met, the warm-up can be retried twice. If it is failed a third time, the user is given the option of quitting the test or proceeding anyway. At the completion of a battery, ARES may be programmed to provide feedback regarding how performance on the just-completed battery of tests compares with past performance by the same subject, or with appropriate normative data.

Figure 4:
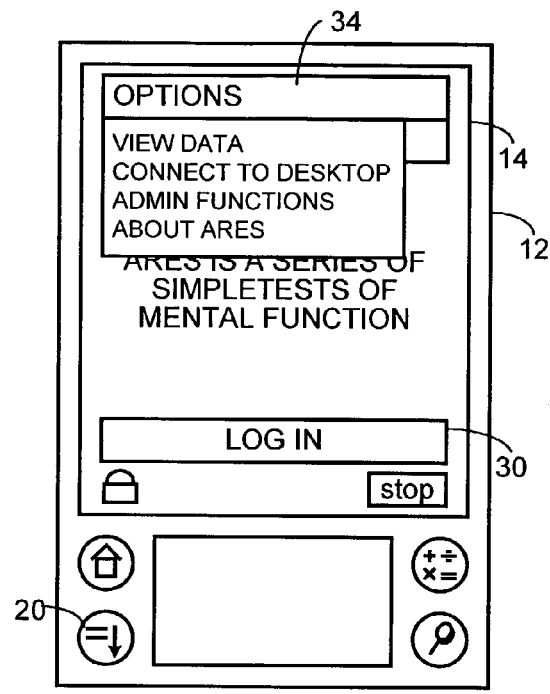
FIG. 4 shows an options screen for a preferred embodiment of an ANAM Readiness Evaluation System.
Figure 5:
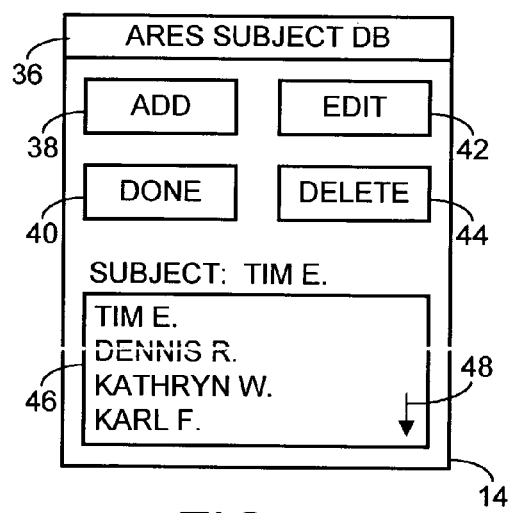
FIG. 5 illustrates an ARES subject database view screen.
Figure 11:
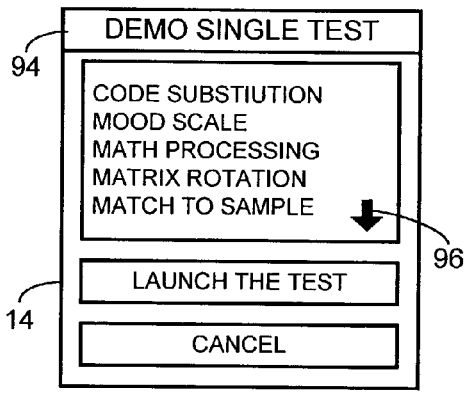
FIG. 11 shows a demonstration single test view screen.

For demonstration purposes, ARES tests may be taken individually. i.e. not as part of a battery, through the "Single Test" button on the Admin Functions screen that is available through the options pull down menu 34, as shown in FIG. 4. FIG. 11 illustrates a demo single test screen 94 of a preferred embodiment. In this mode, the results are saved in a database, as shown in Table 9, but the tests are not configurable. A test is selected on the list, and is launched by tapping the "Launch the Test" button. Although the single test option is available, most subjects will use a pre-specified test battery.

ARES test batteries may consist of up to nine tests. For convenience, several standard test batteries are available as shown in Table 2. These batteries are designed to meet common needs in settings ranging from a relatively complete neuropsychological screen (NeuroCog) to repeated assessment of the cognitive status of military personnel in operational settings (Commander and Warrior). In addition, two demonstration batteries are designed to provide brief samples of the ARES tests and test data. Each test has a small number of trials. The Commander and the two demonstration batteries are automatically installed the first time the ARES program is launched. Custom built batteries can be installed using a data manager program installed on a host computer 116, or by Hot Synching a customized version of the battery database (ARBatDB.PDB) onto the PDA as explained further below.

The NeuroCognitive (NeuroCog) test battery is designed for use by a neuropsychologist who is trained in the use and interpretation of ANAM data. This battery is designed primarily for diagnostic use and medical monitoring of recovery following an insult to the central nervous system. The ARES Commander is designed to provide a brief on-line assessment of the ability to sustain levels of concentration, working memory, and mental efficiency. It is intended for use as a self-monitoring system and is intended for operational commanders in command and control centers as well in field settings. ARES Commander also may be used for similar purposes in other military missions such as sustained flight operations to assess flight crew alertness and readiness. A post-session Performance Index compares performance on the just-completed battery with the subject's prior performance. The ARES Warrior is constructed to provide a neurocognitive screening instrument for use by medics and other medical support personnel who must be able to rapidly assess the mental status of military personnel in field operational medical and combat settings.

Table 8 shows the specifications for the "Commander" test battery Cognitive Status Report of a preferred embodiment of the present invention. Ten scores will be used to derive a performance index (PI) for the test battery, ranging from 0 to 10. Items marked with an asterisk are derived by comparing the current score with scores from three prior sessions. The first session for which a PI will be calculated is session five, and the first four sessions are considered "familiarization" sessions. Data from the first session is not used in calculating the initial baseline set of scores. Sessions two, three, and four are considered "anchor" sessions. These three sessions that are used in deriving the scores, designated the "baseline" sessions, will be the three immediately preceding the current session, with restrictions.

A first restriction for deriving scores is that no session with a performance index less than "7" will be used, and a preceding session is substituted. For example, if the current session is session 10, and the PI on session 8 was 5, the baseline sessions are 9, 7, and 6. A second restriction is that if the average values of the variable in the immediately preceding three sessions is worse than the average of the three anchor sessions, the anchor sessions will be used for that variable. Scores of "9" or greater are considered passing scores, scores of "7" and "8" are marginal, and scores of less than "7" are failure. Other back end specifications of alternate embodiments of the invention may be utilized depending upon the test battery and a pre-determined passing criterion.

PDA operating systems, unlike most computers that use file systems to store programs and data, store all information in "databases" 122. Table 9 lists the databases used by ARES. All ARES tests, with the exception of the Sleep Scale and Mood Scale, use the same format for collecting the data. Data are stored as "records" in the ARDataDB database on the PDA. Each record contains the data from a single test, subject, and administration (session). Data elements (fields) stored for each test are listed in Table 10. Each record consists of four sections. The first section contains housekeeping data for the test. and the last three sections contain numerical results for the entire session, including the first half of the trials in the session and the second half of the trials.

TABLE 8

COMMANDER BATTERY PERFORMANCE INDEX

| TEST | VARIABLE | CALCULATIONS | PASSING CRITERION (PASS-1, FAIL = 0) |
|---|---|---|---|
| Sleep Scale | Rating | none | Absolute score of 4 or less |
|  | *Response Time | Mb = average of the baseline response times (3 scores) Rc = response time of current session | Rc greater than 1 sec and less than 2 times Mb |
| Simple RT | *Median RT | Mb = average median RT of baseline sessions Sb = average SD of mean RT of baseline sessions Mc = median RT from current session | Mc less than or equal to (Mb + Sb) |
|  | *SD RT | Sb = average SD of mean RT of baseline sessions Sc = SD of mean RT of current session | Sc less than or equal to 1.5 times Sb |
|  | Bad + ITI | none | 1 or less |
| Running Memory | *Accuracy | Ab = average accuracy of baseline sessions Ac = accuracy on current session | Ac greater than or equal to 0.9 times Ab |
|  | *Median Correct RT | Same as for Simple RT except only correct response trials are used | Mc less than or equal to (Mb + Sb) |
|  | *SD Correct RT | Same as for Simple RT except only correct response trials are used | Sc less than or equal to 1.5 times Sb |
|  | Lapses | none | 3 or less |
|  | Bad + ITI | none | 1 or less |

TABLE 9

ARES OPERATING SYSTEM DATABASES

| DATABASE | CONTENTS |
|---|---|
| ARDataDB | All test results |
| ARSubDB | Subject records |
| ARLinkDB | Battery control data |

TABLE 9-continued

ARES OPERATING SYSTEM DATABASES

| DATABASE | CONTENTS |
| --- | --- |
| ARBatDB | Configured batteries of ARES tests |
| ARKeyDB | ARES access mode, start date, and stop date |

Referring to Table 10, "Impulsive R's" of the "Battery Version" row are responses within 100 ms of the stimulus onset. These responses are too quick to be processed by the human brain and thus, are not valid. These responses are not included in counts of errors and/or correct responses. "Inter trial R's" located in the "Subject ID" row of Table 10 are key presses between stimuli when the screen is blank. The Repetition Number tracts repetition within the same battery. Random number seed is the session number for the preferred embodiment, but an optional increment may be added for other embodiments. Start time and end time are seconds since Jan. 1, 1904. Spare data variables may be used by some tests that do not fit the normal test template, e.g., sleep scale. "Thruput" in the "Spare5" row is the number of correct responses per minute of available response time, i.e., excluding inter-trial intervals.

TABLE 10

DATA RECORD FIELDS

| HOUSEKEEPING INFORMATION | ENTIRE SESSION | FIRST HALF OF TRIALS | SECOND HALF OF TRIALS |
| --- | --- | --- | --- |
| TEST NAME | RESPONSES | RESPONSES | RESPONSES |
| TEST VERSION | CORRECTS | CORRECTS | CORRECTS |
| BATTERY NAME | ERRORS | ERRORS | ERRORS |
| BATTERY VERSION | IMPULSIVE R'S | IMPULSIVE R'S | IMPULSIVE R'S |
| ARES VERSION | LAPSES | LAPSES | LAPSES |
| SUBJECT ID | INTER-TRIAL R'S | INTER-TRIAL R'S | INTER-TRIAL R'S |
| SESSION NO. | AVG COR RT | AVG COR RT | AVG COR RT |
| REPETITION NO. | AVG ERR RT | AVG ERR RT | AVG ERR RT |
| RANDOM NO. SEED | AVG ALL RT | AVG ALL RT | AVG ALL RT |
| START TIME | SD COR RT | SD COR RT | SD COR RT |
| END TIME | SD ERR RT | SD ERR RT | SD ERR RT |
| SPARE1 | SD ALL RT | SD ALL RT | SD ALL RT |
| SPARE2 | MEDIAN COR RT | MEDIAN COR RT | MEDIAN COR RT |
| SPARE3 | MEDIAN ERR RT | MEDIAN ERR RT | MEDIAN ERR RT |
| SPARE4 | MEDIAN ALL RT | MEDIAN ALL RT | MEDIAN ALL RT |
| SPARE5 | THRUPUT | THRUPUT | THRUPUT |

Figure 8:
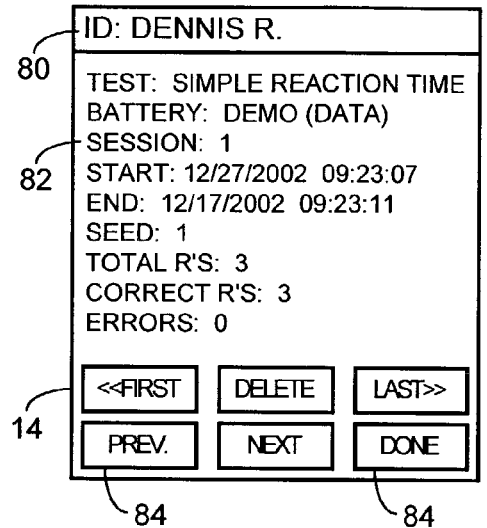
FIG. 8 illustrates an identification view screen.

As shown in FIG. 4, the options menu 34 is viewed by tapping the menu icon 20 at the lower left corner of the PDA OS screen 12. The "View Data" option allows the user to display data. When the display data screen 80 is activated, as shown in FIG. 8, the last record 82 to be recorded, that is, the data from the most recent test run, is displayed first. Buttons 84 are provided to navigate between records. The display data screen 80 of a preferred embodiment does not display the partial-session data. This information is available when the data are downloaded to a host computer 116. The display data screen 80 also enables administrators to delete individual records from the database if ARES is "unlocked" by entering a password.

Continuing with the options menu 34 of FIG. 4, the "Connect to Desktop" option is selected for transferring data to the host computer 116. The "Admin Functions" option provides a password-controlled access to selected functions. Tapping the padlock icon 32 also accesses this function. The "About ARES" screen shows the ARES version number and credits for the ARES software.

The ARES Data Manager program 150 illustrated in FIG. 16 is loaded onto the host computer 116, and has several functions. The program 150 retrieves test and subject data from the PDA using the button in the action field 154. The retrieved data is stored in the ARES.MDB database, which is a Microsoft Access Database file on the host computer 116. The data manager 150 also provides access to the ARES.MDB database file to view and select data 156 for further analysis. Subject information in the ARES.MDB database may be viewed and edited. Custom test batteries may be installed on and removed from the PDA 10. The plot data in the file menu 153, provides access to a window for generating graphical plots of selected variables from the ARES.MDB archive file.

All of the data in the ARDataDB and ARSubjDB databases on the PDA 10 may be transferred to the host computer/desktop 116. The data is displayed in a window 156 at the bottom of the screen, as shown in FIG. 16. Each line in this table contains the data for a single test, except that "startsec" has been converted to the actual date and time that the test started, as shown in the "Start" column. and the test duration in the "Dur" column is calculated by subtracting "startsec" from "endsec". Values that are not applicable or missing for some reason, e.g., mean error RT when no errors were made, are coded as an asterisk "*". The "Subject" and "Test" boxes may be used to select the data displayed in the table. The data displayed in the table can be copied to a Windows Clipboard as tab-delimited text by choosing Copy from the main menu 152, or by typing CTRL+C. The copied data can then be pasted into other Windows applications, such as MS Excel, for further processing.

Downloaded data are automatically saved to a file in the "data" subdirectory of the directory in which the data manager program 150 is located. The file name is the date and time of the download (mmddyy_hhmmss), and the file type, that is, the file name "extension", is "ARD". The .ARD file is a binary file that can be read with the data manager program 150 by choosing File and then Open from the main menu, or by clicking the Load File button. Both the data and the subject information from the PDA 10 are also inserted into the ARES.MDB Microsoft Access database when the data are downloaded. This feature permit sophisticated users to easily extract information of interest from large data sets, to combine data sets, and to partition data to suit investigational or clinical needs. If the data are already present in ARES.MDB, they will not be duplicated, permitting repeated downloads from the same PDA 10 without clearing the database on the PDA. The ARES.MDB database is accessed by selecting the View Archive from the main menu to display the entire data table from the ARES.MDB database. This table can be sorted on any variable by selecting a column and clicking one of the Sort buttons. The entire table, or selected rows can be copied to the Windows clipboard and pasted into other Windows applications.

Figure 17:
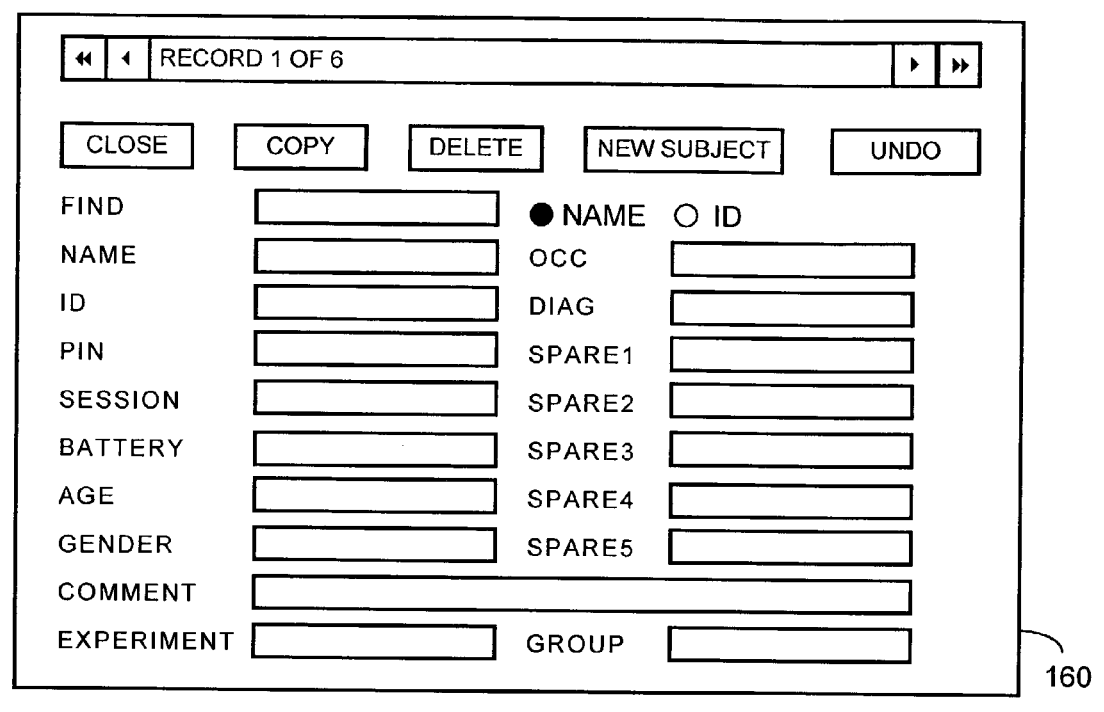

When a subject is registered in ARES, a minimal amount of information is required. To view and edit this information, the Subject Database is selected from the main menu 152 of the data manager program window 150. The panel 160 shown in FIG. 17 provides complete access to the Subjects data table of ARES.MDB. The user can navigate between records, i.e, subjects, using the arrow buttons at the top of the panel. Searches can be performed for subjects by name or ID by selecting the appropriate option button, and by entering the beginning characters of the name or ID in the Find box. Any changes made to any of the fields on this panel are immediately transferred to the database. Until a new record is loaded, clicking the Undo button will reverse any changes that are made. This panel 160 provides several additional fields that can be useful for identifying and classifying subjects. Spare1 through Spare5 are for numerical values. The Comment field will accept up to eighty (80) characters, and the Experiment and Group fields will accept up to twenty-five (25) characters each. The copy button places the contents of all the fields on the Windows Clipboard so the data can be pasted into other Windows programs.

To install, list, or remove custom test batteries on the PDA 10, Battery Manager is selected from the main menu 152. Custom batteries are distributed as "*.ARB" files. For example, NeuroCog.ARB, Commander.ARB, and Warrior.ARB are placed in the ARES folder when the data man program is installed. FIG. 18 illustrates the battery manager window 170. The Select ARB Battery button or the menu File and Open ARB battery is used to locate the desired file for installation. The tests in the battery will be listed in the "Tests" box 172. The properties of each test may be listed in the "Test Parameters" box 174 by clicking the test name. By selecting File and Print ARB Battery or by clicking the print button, a hard copy of the battery with all of the test parameters may be printed. Clicking the copy button puts a copy of the battery with all of the test parameters on the Windows Clipboard. The Battery Manager window 170 further provides buttons for installing the battery on the PDA, for listing the batteries on the PDA, and for deleting a battery from the PDA.

Figure 19:
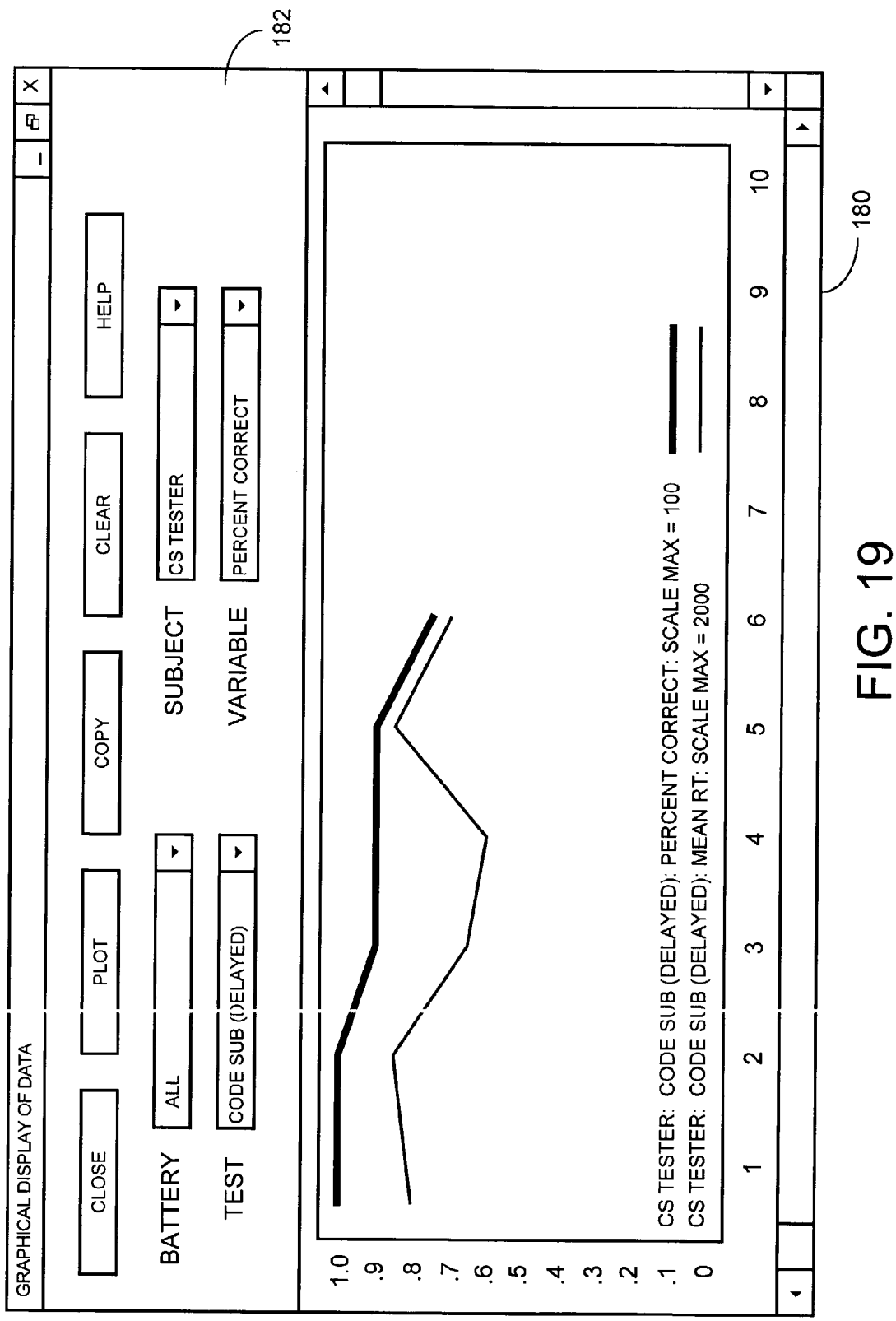
FIG. 19 shows an ARES data management data plotting screen.

The data manager program 150 can produce graphical plots of data from the ARES.MDB data table. To open the plot screen, Plot Data is selected from the main menu 152. FIG. 19 illustrates the graphical display of data window 180. To plot data from the ARES.MDB archive, a Battery, Subject, Test, and Variable are selected form from the drop-down lists 182. The Battery, Test and Subject lists are populated with all of the instances of the respective items from the ARES.MDB data table. The Variable drop-down list allows variables to be selected for the entire session, for the first half of the session (1), or for the second half of the session (2). These variable include Mean Correct Response Times (RT), SD of Correct RT, Median of Correct RT, Percent correct, Lapses, and Thruput. Up to ten different variables can be displayed on the same graph in the preferred embodiment of the invention. Further, the plot window can be minimized, moved, and maximized, and the properties of each variable can be changed by right-clicking on the variable in the legend.

Figure 9:
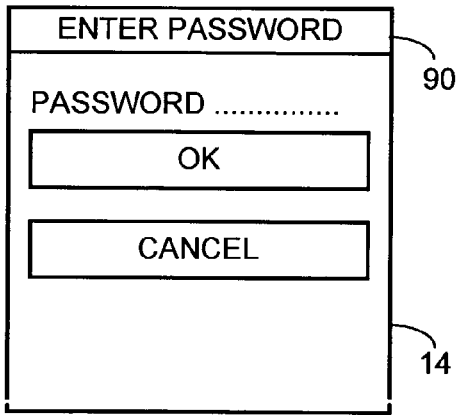
FIG. 9 shows a password view screen.
Figure 10:
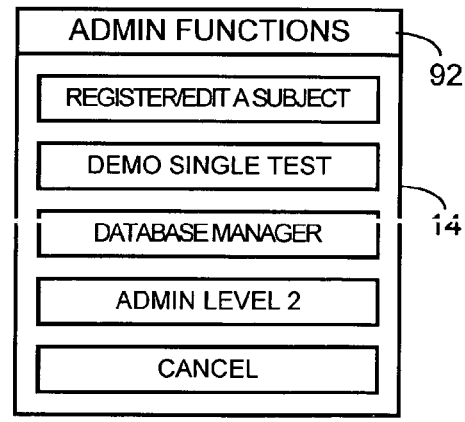
FIG. 10 shows an administration functions view screen.
Figure 12:
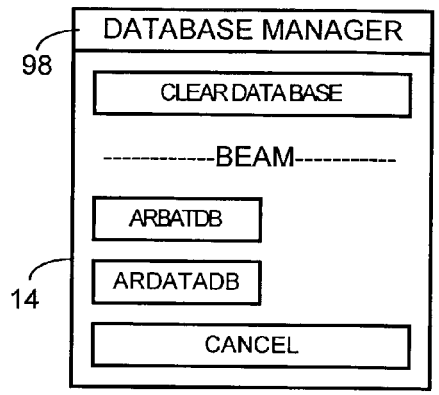
FIG. 12 shows a database manager view screen.

ARES Administration Functions, illustrated in FIGS. 9, 10, 11, and 12 are accessed through the options menu 34 of the main ARES window shown in FIG. 4. To access the Administration Functions, the user must enter a password on the password screen 90, as shown in FIG. 9. The password is provided to authorized individuals, only. When this password is successfully entered, the Admin functions are "unlocked" and need not be entered again until ARES is closed. An open padlock 32 on the main ARES screen indicates the unlocked state. Once a correct password is entered, the admin functions screen 92 of FIG. 10 is activated. The first button launches the AresSub application for registering new subjects and for modifying the records of existing subjects. The Demo Single Test button allows a single test module to be run for demonstration purposes as shown in FIG. 11. The Database Manager screen of FIG. 12 is provided for maintenance of the ARES databases on the PDA. The clear data base button allows a data database (ARDataDB) to be deleted from the PDA.

Beam buttons use the Palm OS "Beam" function to transfer the data and battery (ARBatDB) databases to another PDA. These functions are used when setting up PDA.

Although a preferred embodiment of the invention has been described above by way of example only, it will be understood by those skilled in the field that modifications may be made to the disclosed embodiment without departing from the scope of the invention, which is defined by the appended claims.

We claim:

1. An assessment and rehabilitation system for cognitive testing of a plurality of users, the system comprising:
   a handheld computer comprising:
      a CPU operating an executive program for controlling a plurality of modules comprising:
         a plurality of test modules, each executing a specific individual test on the handheld computer to test a cognitive attribute of a user;
         a plurality of test batteries each comprising one or more specified test modules, the specified test modules being selectively chosen for each test battery to test a respective cognitive attribute of one or more of the plurality of users, at least one test battery having at least two specified test modules for testing different cognitive attributes, wherein the plurality of test modules generate a test stimuli;
         at least one registration module for registering each of the plurality of users;
         a plurality of interpretive modules for interpreting results of the test batteries, wherein the interpretive modules compare the user's current test performance with normative data, the user's previous test results and passing criterion for each test module in order to determine the current test results for the test batteries; and
         at least one report module for immediately generating a cognitive status report for reporting the test battery results as determined by the plurality of interpretive modules;
      a screen for displaying test stimuli and test battery results; and
      an input portion permitting each of the users to register with the at least one registration module, select one or more test batteries for administration by the executive program, and respond to the stimuli.

2. The assessment and rehabilitation system of claim 1, wherein the plurality of test modules comprises one or more of a code substitution module, a logical relations module, a mood scale module, a mathematical processing module, a matrix rotation module, a matching to sample module, a running memory module, a simple reaction time module, a sleep scale module, and a memory search module.

3. The assessment and rehabilitation system of claim 2, wherein at least one test battery is for testing readiness to stand duty of a user of the plurality of users.

4. The assessment and rehabilitation system of claim 3, wherein the at least one test battery is a NeuroCognitive test battery for one of diagnostic use and medical monitoring of recovery, the NeuroCognitive test battery comprising the sleep scale module, the mood scale module, the simple reaction time module, the code substitution module, the mathematical processing module, the matching to sample module, the logical relations module, the code substitution module and the memory search module.

5. The assessment and rehabilitation system of claim 3, wherein the at least one test battery is a commander test battery for providing a brief on-line assessment of a user of the plurality of users, the brief on-line assessment for testing the user's ability to sustain levels of one or more of concentration, working memory and mental efficiency.

6. The assessment and rehabilitation system of claim 5, wherein the commander test battery comprises the sleep scale module, the simple reaction time module, and the running memory module.

7. The assessment and rehabilitation system of claim 1, wherein the at least one report module generates a cognitive status report for immediate feedback upon completion of at least a subset of the plurality of test modules.

8. The assessment and rehabilitation system of claim 1, further comprising a host computer for executing a plurality of component utilities, the component utilities comprising:

a plurality of communications and data archiving modules for retrieving data from the handheld computer, for archiving data, for assessing data quality, and for installing and managing test batteries on the handheld computer; and a plurality of test battery authoring modules for configuring customized test batteries, the test batteries comprising at least one of the plurality of test modules.

* * * * *